United States Patent [19]

Brambila et al.

[11] Patent Number: 6,071,985
[45] Date of Patent: Jun. 6, 2000

[54] CATALYTIC CURING AGENT FOR RESINS AND METHOD FOR MAKING THE SAME

[76] Inventors: Rene Becerra Brambila; German Maya Hernandez, both of Paseo de la Reforma No. 30, Third Floor, 06600 Mexico, D.F., Mexico

[21] Appl. No.: 09/154,018

[22] Filed: Sep. 16, 1998

Related U.S. Application Data

[63] Continuation of application No. 08/899,771, Jul. 24, 1997, abandoned.

[51] Int. Cl.[7] .......................................................... B22C 1/22

[52] U.S. Cl. ............................ 523/143; 523/102; 264/83; 264/219; 264/225; 264/331.22

[58] Field of Search ..................................... 523/143, 102; 264/219, 83, 225, 331.22

[56] References Cited

U.S. PATENT DOCUMENTS

| | | | |
|---|---|---|---|
| 3,429,848 | 2/1969 | Robins | 523/143 |
| 3,624,122 | 11/1971 | Kamal et al. | 560/355 |
| 5,451,446 | 9/1995 | Kincaid et al. | 428/143 |

*Primary Examiner*—Mark L. Warzel
*Attorney, Agent, or Firm*—Tod R. Nissle, P.C.

[57] ABSTRACT

Dimethylpropylamine is provided. This new amine surprisingly has a significantly less offensive odor and is considerably less prone to be impregnated in or coat the skin and clothing than are other amines which are utilized to catalyze phenol formaldehyde and polyisocyanate resins during the production of sand cores in the "Cold Box Process". Dimethylpropylamine also cures phenol formaldehyde and polyisocyanate resins at a surprisingly rapid rate. Dimethylpropylamine is produced utilizing a reaction mixture which includes Dimethylamine and Propyl alcohol such that the molar ratio of Dimethylarine to Propyl alcohol is in the range of 0.07 to 0.5.

9 Claims, No Drawings

CATALYTIC CURING AGENT FOR RESINS AND METHOD FOR MAKING THE SAME

This is a continuation, of application Ser. No. 08/899,771, filed Jul. 24, 1997 now abandon.

This invention relates to a catalytic curing agent for curing resins and to a method for making the same.

More particularly, the invention relates to an amine curing agent for use in curing phenol formaldehyde and polyisocyanate binding resins which are used as agglutinating agents during sand core making, especially during the Cold Box Process utilized in foundries.

In a further respect, the invention relates to an amine curing agent of the type described which rapidly catalyzes binding resins and which does not possess the strong, irritating, and itching ammonia odor associated with Trimethylamine, Dimethylethylamine, and Triethylamine.

The use of Trimethylamine (N,N-Dinethyimethanamine—$C_3H_9N$), Dimethylethylamine (N,N-Dimethylethylamine—$C_4H_{11}N$), and of Triethylamine (N,N-Diethylethanamine—$C_6H_{15}N$) as curing agents has long been known. See, for example, U.S. Pat. Nos. 3,429,848; 3,485,797; 3,676,392; and, 3,432,457. These tertiary amines are sometimes utilized with metal salts and provide a fast curing of phenol formaldehyde and polyisocyanate resins at room temperature. The Dimethylethylamine provides a significantly faster curing rate than Triethylamine. This is believed due to Dimethylethylamine's lower molecular weight of 73. In comparison. the molecular weight of Triethylamine (101) is believed to inhibit and slow the curing process.

The tertiary amines noted above have undesirable organoleptic characteristics. In particular, the amines have a strong, irritating, itching, and offensive ammonia odor. They irritate the skin, irritate mucous membranes, and are particularly corrosive to soft tissues and eyes. Furthermore, these amines are very easily impregnated in the skin and in the clothing, making a very unpleasant working environment when they are utilized.

Accordingly, it would be desirable to provide for the first time an amine which rapidly catalyzes phenolformaldehyde and polyisocyanate resins and which does not have a strong offensive odor and does not impregnate the skin and clothing.

We have discovered a new amine and method for making the same. We were unable to locate our new amine in databases prepared by the Environmental Protection Agency (EPA) in the United States of America. Consequently, it appears that the new ainine is now for the first time commercially available. The new amine, which we designate N,N-Dimethylpropylamine ($C_5H_{13}N$)(hereafter called Dimethylpropylamine), has the following structure:

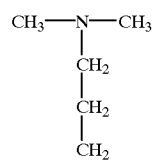

The boiling point of Dimethylpropylamine at one atmosphere pressure is typically in the range of 65 to 68 degrees C. The specific gravity of Dimethyipropylamine at 20 degrees C. is 0.71 to 0.72 grams per cubic centimeter. Dimethyipropylamine is a clear transparent liquid (APHA Color of 10).

We encountered surprising and unexpected results in connection with Dimethylpropylamine. First, in comparison to tertiary amines which have been utilized for many years in the Cold Box process, Dimethyipropylamine has an odor which is substantially less offensive and which is less likely to impregnate the skin and clothing.

Yet another surprising and unexpected result appeared in connection with the use of Dimethyipropylamine. Dimethylpropylamine appears to cure phend formaldehyde and polyisocyanate resin fast as, or nearly as fast as, Dimethylethylamine. This result was unexpected because the molecular weight of Dimethylpropylamine (87) is significantly greater than the molecular weight of Dirnethylethylammne (73). An amine with a lower molecular weight ordinarily is preferred because the lower molecular weight facilitates diffusion of the amine through sand when the amine is in a gaseous state.

Dimethylpropylamine can be used in a liquid state or in a gaseous state and in any desired predetermined concentration. As is known, the time required to cure a phenol formaldehyde or polyisocyanate resin can vary depending on several factors, including, by way of example and not limitation, the volume of sand in a mold, the shape of the mold, the concentration of the amine in the gas mixture, the location of the inlet ports to distribute the amine through the mold, and the rate at which the amine flows through or into the mold (i.e., the pressure under which the amine is injected in the mold). Given parameters which typically are encountered during sand core making, the time required for Dimethylpropylamine to cure phenol formaldehyde and polyisocyanate resins during casting is presently typically in the range of one to sixty seconds.

During the Cold Box Process, sand is mixed with phenolformaldehyde and polyisocyanate resins. The resulting sand—resins mixture is blown into a steel mold, after which a catalyst mixture including an amine catalyst and an inert carrier is injected into the steel mold to cause the resins to harden and to bind together the particles comprising the sand. The catalyst is usually, although it need not be, a combination of one inert gas and one amine gas. The inert gas typically comprises nitrogen. The amine can comprise one of the prior art tertiary amines noted above, but in accordance with the invention, preferably comprises Dimethylpropylamine.

The boiling point of the amine utilized to cure the phenol formaldehyde and polyisocyanate resins is preferably below 100 degrees C. to permit ready evaporation and to achieve a satisfactory concentration of amine in the amine—nitrogen mixture injected into the steel mold. A boiling point below 100 degrees also helps to avoid condensation of the amine when it contacts the steel mold. The 88 degrees C. boiling point of Triethylamine is probably the highest practical boiling point because during very cold winter days (1) the Triethylamine tends to condense out of the gas mixture in the piping which carries the amine—nitrogen mixture to the steel mold and, (2) in addition, badly cured spots are found in sand cores produced in the steel mold.

On the other hand, the boiling temperature of the amine preferably must be high enough to facilitate handing of the amine. Trimethylamine is a gas at normal ambient temperatures, which makes it difficult to handle.

The molecular weight of the amine must be low enough to permit ready diffusion of the amine through sand in the steel mold, especially into the corners of the mold. The molecular weight of Triethylamine (101) is probably about the greatest permissible molecular weight.

While phenolformaldehyde is presently preferred, any phenol aldehyde resin can be utilized in the practice of the invention. The preferred is phenols are those which are (1)

unsubstituted in the para-position, as well as in the ortho-positions, and (2) which have positions which can be substituted only with substituents with one to six carbon atoms. The most preferred phenol is unsubstituted phenol.

Any aldehyde with a hydrocarbon radical of one to eight atoms can be utilized in the practice of the invention. The most preferred aldehyde is, however, formaldehyde.

Any aliphatic, cycloaliphatic, or aromatic polyisocyanate having preferably two to five isocyanate groups can be utilized in the practice of the invention, and, if desired, a mixture of polyisocyanates can be used. The preferred polyisocyanates are aromatic and particularly diphenylmethane diisocyanate, triphenylmethane triisocyanate, and methylene bisphenylisocyanate.

In the Cold Box process, any tertiary amine with a high molecular weight and with a boiling point above 100 degrees C. is difficult to utilize. The Cold Box process is utilized when a high production rate is desired, and the normal curing time of the resins when catalyzed with an amine is typically around three seconds sometimes even under one second depending on the size and shape of the sand core.

Nitrogen is the gas most widely utilized to carry an amine, particularly when a bubbler type gas mixture generator is utilized, but carbon dioxide is less expensive and is sometimes utilized. When an injector type gas generator is employed, only air is used as the gas which carries the amine.

When a bubbler type generator is utilized, the amine concentration is determined by liquid-gas equilibrium, but by adjusting the pressure and temperature a concentration of between 10% to 15% by weight amine in the amine-gas mixture is typically obtained. Similar results are achieved for an injector type generator, in which a small amount of liquid amine is pumped and sprayed into a hot air stream.

The concentration of water in an amine can vary as desired but is preferably kept below 0.2% by weight. If the impurity in the amine of the invention is a tertiary amine, any adverse effects will be minimal if the boiling point and average molecular weight of the amine of the invention are not greatly affected. Primary and secondary amines can catalyze the curing reaction of phenol-aldehyde and polyisocyanate resins but at a slower rate than a tertiary amine. Therefore the concentration of primary and secondary amine impurities in the amine of the invention is preferably maintained at 0.5% by weight or less. The amine of the invention typically includes less than 0.2% by weight water and less than 0.5% by weight of primary, secondary and tertiary amine impurities.

During high production core processes (where resins when catalyzed with the amines typically cure in eight seconds or less) the amine of the invention is only utilized in its gaseous state. When the amine of the invention is utilized as a liquid, a liquid carrier can be utilized but is not required for the amine.

One reason that low concentrations of water in the amine of the invention are important is that water and polyisocyanate react and form a stable compound. The formation of such a stable compound interferes with curing of phenol formaldehyde and polyisocyanate resins during the Cold Box process by preventing the polyisocyanate from reacting with the phenolic resin. The present invention also pertains to the manufacturing process of Dimethylpropylamine by the reaction of Dimethylamine and Propyl alcohol.

There has not been reported a process for reacting Dimethylamne and Propyl alcohol in the presence of Hydrogen and a hydrogenation catalyst, and in particular utilizing cobalt and nickel catalysts. Although the catalytic amination of alcohols has been widely reported and the reaction of secondary amines with alcohols has been already described, a cobalt or nickel catalyst apparently has never been utilized for these purposes.

The invention consists of the reaction of Dimethylamine and Propyl alcohol, in gaseous phase, over a catalyst containing cobalt or nickel, cobalt oxide or nickels oxides and various additives. This reaction takes place at a pressure between one and twenty kilograms per square centimeter, and at a temperature between 100 and 200 degrees C. Hydrogen is utilized in such quantities that the molar ratio of Hydrogen to the alcohol is maintained between 3 and 10. The molar ratio of Dimethylamine to Propyl alcohol is maintained between 0.07 and 0.5, and the space velocity of the gaseous feeds into the catalyst bed is maintained between 500 and 2000 $hour^{-1}$. The space velocity is the flow rate into the reactor of the feed gases (Hydrogen, Propyl alcohol, Dimethylamine) in cubic meters per hour divided by the volume in cubic meters of the catalyst in the reactor; hence, the units of measurement of $hour^{1}$.

It is possible to obtain 100% conversion of the dimethylamine and a yield of more than 95%. Otherwise, several by-products are formed in the reaction, reducing the yield and rate of reaction. These by-products are formed due to the deproportionation reaction of Dimethylamine, in which Ammonia, Monomethylamine, and Trimethylamine are produced giving way to several by-products from the cross-reactions between Ammonia, Monomethylamine, Trimethylamine and Propyl alcohol.

The following examples are, without limitation, provided to illustrate the practice of the invention:

EXAMPLE 1

A reduced pelleted nickel hydrogenation catalyst is placed in a reactor and activated. The activation of catalysts with nitrogen, hydrogen and/or other components is well known in the art and will not be detailed herein. Hydrogen is fed into the pressurized reactor at a pressure between 10 to 20 kilograms per square centimeter. Dimethylamine and Propyl alcohol (propanol) are fed into the reactor in a gaseous state carried by the hydrogen. The Hydrogen—Dimethylamine—Propanol feed enters the reactor. The proportions of Dimethylamine and Propyl alcohol in the reactor feed are such that the molar ratio of the total number of moles of Dimethylarine to the total member of moles of Propyl alcohol is 0.1. The molar ratio of Dimethylamine to Propyl alcohol is critical in the practice of this invention. In the practice of the invention a molar ratio of Dimethylamine to Propyl alcohol in the range of about 0.07 to 0.5 is acceptable. Such a molar ratio is significantly different from molar ratios of 1.0 or more which typically are encountered in the production of other amines. The temperature at the inlet in the reactor is 130 degrees C. The Hydrogen, Propanol, and Dimethylamine enter the reactor at the inlet at a temperature of 130 degrees C. (or any other desired temperature in the range of 100 degrees C to 200 degrees C). The temperature at the outlet is 145 degrees C. The spatial velocity of the Hydrogen—Propyl alcohol—Dimethylamine through the reactor is 1000 $hour^{1}$. The temperature at the reactor outlet is monitored, and when the temperature begins to exceed 145 degrees C, the temperature at the reactor inlet is reduced to maintain the outlet temperature at 145 degrees C. (or at any other desired temperature in the range of 100 degrees C. to about 200 degrees C). When the temperature in the reactor is greater than about 150 degrees C, the quantity of Dimethylpropylamine produced from a mole of Dimethylamine introduced into the reactor decreases. Consequently, while the reactor can be operated at up to about 200 degrees C, the preferred temperature in the reactor is in the range of 120 to 150 degrees C. At temperatures less than 120 degrees C the quantity of Dimethylpropylamine produced from a mole of Dimethylamine also decreases.

The general reaction that, with the aid of the nickel catalyst, takes place between the propanol and the Dimethylamine is believed to be:

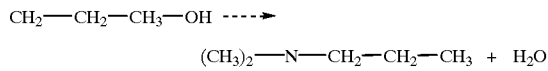

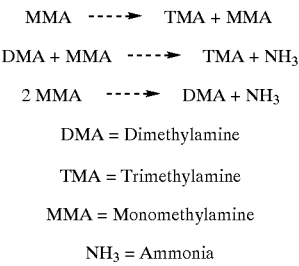

The deproportionation reaction of Dimethylamine yields a mixture of Trimethylamine, Monomethylamine and Ammonia according to the following reactions:

$$MMA \longrightarrow TMA + MMA$$

$$DMA + MMA \longrightarrow TMA + NH_3$$

$$2\,MMA \longrightarrow DMA + NH_3$$

DMA = Dimethylamine

TMA = Trimethylamine

MMA = Monomethylamine $NH_3$ = Ammonia

The Ammonia and Monomethylamine formed by the deproportionation of the Dimethylamine are believed to react with Propyl alcohol to form Monopropylamine, Dipropylamine, Monomethylpropylamine, and Methyldipropylamine.

An analysis of the crude product revealed that for each one mole Dimethylamine and ten moles of Propyl alcohol introduced into the reaction chamber, about 82 pounds of Dimethylpropylamine are produced, and four pounds of byproducts are produced.

EXAMPLE 2

Example 1 is repeated, except that the temperature at the inlet of the reactor is 150 degrees C. and the temperature at the outlet is 180 degrees C. Similar results are obtained, except the quantity of Diinethylpropylamine produced from each mole of Dimethylamine introduced in the reactor is reduced.

EXAMPLE 3

Example 1 is repeated, except that the nickel catalyst is replaced with a cobalt catalyst. Similar results are obtained.

EXAMPLE 4

Example 1 is repeated, except that a copper-chromite catalyst is utilized in place of the nickel catalyst. Similar results are obtained.

EXAMPLE 5

Example 1 is repeated, except that the molar ratio of Dimethylamine to Propyl alcohol in the feed stream to the reactor is 0.2 instead of 0.1. Similar results are obtained.

EXAMPLE 6

Example 1 is repeated, except that the molar ratio of Dimethylamine to Propyl alcohol in the feed stream to the reactor is 0.4 instead of 0.1. Similar results are obtained.

EXAMPLE 7

Example 1 is repeated, except that the spatial velocity is 1500 hour$^{-1}$ instead of 1000 hour$^{-1}$. Similar results are obtained, however, the conversion of Dimethylamine to Dimethylpropylamine is, in comparison to the original spatial velocity of 1000 hour$^{-1}$, diminished and less Dimethylpropylamine is produced for each mole of Dimethylamine introduced into the reactor.

EXAMPLE 8

A test was carried out in the plant of a customer. Sand cores were produced in the plant by curing sand—resins mixtures. In the test Dimethylpropylamine was utilized in place of the Dimethylethylamine normally used in the customer's plant. The test was carried out under the same operating conditions used when the customer utilized Dimethylethylamine. These conditions are shown in the following Table I.

TABLE I

| | |
|---|---|
| At the amine-nitrogen generator: | |
| Type: | Injector |
| Operating pressure: | 30 psig |
| Operating temperature: | 60 degrees C. |
| At the core producing machine: | |
| Core weight: | 25 pounds |
| | (3 cores per cycle) |
| Amount of phenol formaldehyde resin: | 1% by weight of sand |
| Amount of polyisocyanate resin: | 1% by weight of sand |
| Purge time: | 5 seconds |
| Gasing time: | 0.3 seconds |
| Total cycle time: | 70 seconds |
| At the laboratory test equipment: | |
| Sample type: | Dogbone(AFS specification) |
| Sample weight: | 100 grams |
| Amine gas pressure: | 45 psig |
| Amine gas temperature: | 50 degrees C. |
| Purge time: | 5 seconds |
| Gasing time: | 3 seconds |

The quality of the cores produced during the Dimethylpropylamine test was as good as when the Dimethylethylamine was utilized. Therefore, all the cores produced during the Dimethylpropylamine test were sent to metal pouring, which is the following step in the casting production process, with no reported defects in the sand cores and without casting defects related to core problems.

The laboratory test equipment was utilized to evaluate the core production process. The equipment tested the tensile resistance of cured sand cores and, each time a new sand-resins mixture load was prepared, tested the permeability of the sand-resins mixture.

The laboratory tests were carried out evaluating cured sand cores produced with Dimethylethylamine cured sand—resins mixtures and produced with Dimethylpropylamine cured sand—resins mixtures. The test results for Dimethylpropylamine were nearly identical to those obtained with Dimethylethylamine. The average tensile resistance of a cured sand core produced when Dimethylpropylamine was utilized was 231.5 pounds per square inch (the minimum acceptable tensile strength is 120 pounds per square inch), while the average tensile strength when Dimethylethylamine was utilized was 235 pounds per square inch.

During the use of Dimethylpropylamine during the test, the odor offensiveness of Dimethylpropylamine and Dimethylethylamine and the tendency of both amines to impregnate skin and clothing were compared. After the test utilizing Dimethylpropylamine was completed, plant personnel including four operators, the core production manager, and the laboratory manager were queried in this respect. All of them responded that the odor in the core production area was. when Dimethylpropylamine was utilized in place of Dimethylethylamine, greatly reduced some even suggested that they did not defect any amine odor in the ambient air in the plant, possibly due to the various other odors encountered in the ambient air of a foundry. The plant personnel were also asked to compare the residual odor which remained on their skin and clothing after their work shift was completed. They commented that there was no amine odor left on their clothing or skin. In comparison, when Dimethylethylamine is utilized, a residual odor always remains on clothing and skin.

EXAMPLE 9

A "Bulk curing test" was carried out in the laboratory of a customer. The "Bulk curing test" measures the curing efficiency of an amine catalyst.

In the "Bulk curing test" a fixed amount of sand—resins mixture with a predetermined amount of resins per mass unit of sand (normally between 0.5 and 2% by weight of each resin based on the amount of sand mixed) is put in a long cylindrical shaped mold, the amine is poured as liquid on top of the sand—resins cylinder and a stream of carrier gas (normally nitrogen) at a fixed and predetermined rate is passed through the cylinder during a fixed time. The result of the test is the measurement of the length of the sand—resins mixture which is cured.

Dimethylpropylamine, Dimethylethylamine, and Triethylamine were tested. The relative value of the cured length was determined for each and the results were as follows:

| | |
|---|---|
| Dimethylethylamine | 80 |
| Dimethylpropylamine | 75 |
| Triethylamine | 60 |

From these test results it has been concluded that the effectiveness of Dimethylpropylamine in curing resins is comparable to that of Dimethylethylamine, especially when very short gasing and purge times are used and the difference in curing effectiveness is too small to affect the cycle time.

EXAMPLE 10

Example 8 is repeated, except that formaldehyde is replaced with another aldehyde having a hydrocarbon radical of one to eight atoms. Similar results are obtained.

EXAMPLE 11

Example 8 is repeated, except that formaldehyde is replaced with another aldehyde different from the aldehyde of Example 10 and having a hydrocarbon radical of one to eight atoms. Similar results are obtained.

EXAMPLE 12

Example 8 is repeated. The polyisocyanate utilized is diphenylmethane diisocyanate. Similar results are obtained.

EXAMPLE 13

Example 8 is repeated. The polyisocyanate utilized is triphenylmethane triisocyanate. Similar results are obtained.

EXAMPLE 14

Example 8 is repeated. The polyisocyanate utilized is methylene bisphenylisocyanate. Similar results are obtained.

Having described my invention in such terms as to enable those skilled in the art to make and practice the invention,

We Claim:

1. A process for reducing in a plant a strong, irritating, itching, and offensive odor produced when sand cores are produced using amines, said odor producing residual odor on skin and clothing, and skin and mucous membrane irritation, said process including the steps of
(a) mixing phenol-aldehyde and isocyanate resins with sand;
(b) charging the sand into a mold; and
(c) curing and hardening said resins and reducing in the plant
(i) the production of strong, irritating, itching, and offensive amine odor,
(ii) residual amino odor on the skin and clothing, and
(iii) skin and mucous membrane irritation, by introducing into the mold in the plant Dimethylpropylamine instead of an amine selected from the group consisting of Trimethylamine, Dimethlethylamine, and Triethylamine.

2. A process for preventing in a plant residual amine odor on clothing and skin during the production of sand cores with amines, said process including the steps of
(a) mixing phenol-aldehyde and isocyanate resins with sand;
(b) charging the sand into a mold; and
(c) curing and hardening said resins and preventing in the plant residual amine odor on clothing and skin by introducing into the mold Dimethypropylamine instead of an amine selected from the group consisting of Trimethylamine, Dimethylethylamine, and Triethylamine.

3. A process for producing sand cores in a plant and preventing strong, irritating, itching, and offensive residual amine odors on clothing and skin in the plant including the steps of
(a) mixing phenol-aldehyde and isocyanate resins with sand;
(b) charging the sand into a mold; and
(c) curing and hardening said resins and preventing the strong, irritating, itching, and offensive residual amine odors on clothing and skin by introducing into the mold in the plant Dimethylpropylamine instead of an amine selected from the group consisting of Trimethylarnine, Dimethylethylamine, and Triethylamine.

4. The process of claim 1 wherein said phenol-aldehyde resin is phenol formaldehyde resin and said isocyanate resin is polyisocyanate resin.

5. The process of claim 2 wherein said phenol-aldehyde resin is phenol formaldehyde resin and said isocyanate resin is polyisocyanate resin.

6. The process of claim 3 wherein said phenol-aldehyde resin is phenol formaldehyde resin and said isocyanate resin is polyisocyanate resin.

7. The process of claim 1 wherein the curing efficiency of Dimethylpropylamine is similar to that of Dimethylamine.

8. The process of claim 2 wherein the curing efficiency of Dimethylpropylamine is similar to that of Dimethylamine.

9. The process of claim 3 wherein the curing efficiency of Dimethylpropylamine is similar to that of Dimethylamine.

* * * * *